(12) United States Patent
Marto

(10) Patent No.: US 9,110,071 B2
(45) Date of Patent: Aug. 18, 2015

(54) CHROMATOGRAPHIC COLUMNS WITH INTEGRATED ELECTROSPRAY EMITTERS

(75) Inventor: Jarrod A. Marto, Wayland, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1366 days.

(21) Appl. No.: 12/601,607

(22) PCT Filed: May 27, 2008

(86) PCT No.: PCT/US2008/064845
§ 371 (c)(1),
(2), (4) Date: Mar. 29, 2010

(87) PCT Pub. No.: WO2008/150759
PCT Pub. Date: Dec. 11, 2008

(65) Prior Publication Data
US 2010/0193683 A1    Aug. 5, 2010

Related U.S. Application Data

(60) Provisional application No. 60/932,734, filed on Jun. 1, 2007.

(51) Int. Cl.
*G01N 30/60* (2006.01)
*G01N 30/72* (2006.01)

(52) U.S. Cl.
CPC ........ *G01N 30/6004* (2013.01); *G01N 30/7266* (2013.01); *G01N 2030/6013* (2013.01)

(58) Field of Classification Search
CPC ................. G01N 30/6004; G01N 2030/6013; G01N 30/7266

USPC ....................................... 210/635, 656, 198.2
See application file for complete search history.

(56) References Cited

U.S. PATENT DOCUMENTS

| 4,483,773 | A |   | 11/1984 | Yang |
|---|---|---|---|---|
| 4,793,920 | A |   | 12/1988 | Cortes et al. |
| 4,902,442 | A |   | 2/1990 | Garces |
| 5,378,440 | A | * | 1/1995 | Herbst et al. .................. 423/210 |

(Continued)

FOREIGN PATENT DOCUMENTS

| EP | 0 231 684 | 6/1991 | ............. G01N 30/56 |
|---|---|---|---|
| EP | 1 126 275 | 8/2001 | ........... G01N 27/447 |
| WO | 2007/092227 | 8/2007 | |

OTHER PUBLICATIONS

Ruedi Aebersold et al., "Mass spectrometry-based proteomics", *Nature* vol. 422, pp. 198-207 (2003).

(Continued)

*Primary Examiner* — Ernest G Therkorn
(74) *Attorney, Agent, or Firm* — Fish & Richardson P.C.

(57) ABSTRACT

A method of fabricating a chromatographic column and columns produced by such a method are disclosed. The method includes: (a) obtaining a tube comprising two open ends and a lumen with a diameter of 75 microns or less extending between the two open ends; (b) depositing a liquid silicate composition into the tube lumen at a first open end of the tube; (c) forming a porous ceramic material from the composition in the tube lumen at a location near the first open end such that a space is formed between the ceramic material and the open end that is substantially free of the ceramic material; and (d) forming a tapered emitter having an orifice diameter of less than 3 microns at the first open end.

25 Claims, 7 Drawing Sheets

(56) References Cited

U.S. PATENT DOCUMENTS

| | | | |
|---|---|---|---|
| 5,938,919 | A | 8/1999 | Najafabadi |
| 5,997,746 | A | 12/1999 | Valaskovic |
| 6,190,559 | B1* | 2/2001 | Valaskovic ............... 210/656 |
| 6,670,607 | B2 | 12/2003 | Wood et al. |
| 6,737,640 | B2 | 5/2004 | Kato |
| 2004/0014143 | A1 | 1/2004 | Haskins et al. |

OTHER PUBLICATIONS

Michael P. Balogh, "The Emerging Technologies in the MS Arsenal", *LCGC Asica Pacific*, vol. 8, No. 1, pp. 30-38 (Mar. 2005).

Claudio Borra et al., "Quantitative Analytical Aspects of Reversed-Phase Liquid Chromatography with Slurry-Packed Capillary Columns", *Journal of Chromatography*, No. 385, pp. 75-85 (1987).

Jose Castro-Perez et al., "Increasing throughput and information content for in vitro drug metabolism experiments using ultra-performance liquid chromatography coupled to a quadrupole time-of-flight mass spectrometer", *Rapid Communications in Mass Spectrometry*, vol. 19, pp. 843-848 (2005).

H.J. Cortes et al., "Porous Ceramic Bed Supports for Fused Silica Packed Capillary Columns Used in Liquid Chromatography", *Journal of High Resolution Chromatography & Chromatography Communications*, vol. 10, pp. 446-448 (Aug. 1987).

Ayman el-Faramawy et al., "Efficiency of Nano-Electrospray Ionization", *American Society for Mass Spectrometry*, vol. 16, pp. 1702-1707 (2005).

William E. Haskins et al., "Capillary LC-MS$^2$ at the Attomole Level for Monitoring and Discovering Endogenous Peptides in Microdialysis Samples Collected in Vivo", *Analytical Chemistry*, vol. 73, No. 21, pp. 5005-5014 (Nov. 1, 2001).

Showchien Hsieh et al., "Preparation and Evaluation of Slurry-Packed Liquid Chromatography Microcolumns with Inner Diameters from 12 to 33 μm", *Analytical Chemistry*, vol. 68, No. 7, pp. 1212-1217 (Apr. 1, 1996).

Yasushi Ishihama et al., "Microcolumns with self-assembled particle frits for proteomics", *Elsevier—Journal of Chromatography A*, No. 979, pp. 233-239 (2002).

Alexander R. Ivanov et al., "Low-Attomole Electrospray Ionization MS and MS/MS Analysis of Protein Tryptic Digests Using 20-μm-i.d. Polystyrene—Divinylbenzene Monolithic Capillary Columns", *Analytical Chemistry*, vol. 75, No. 20, pp. 5306-5316 (Oct. 15, 2003).

Karl-Erik Karlsson et al., "Separation Efficiency of Slurry-Packed Liquid Chromatography Microcolumns with Very Small Inner Diameters", *Analytical Chemistry*, No. 60, pp. 1662-1665 (1998).

Robert T. Kennedy et al., "Preparation and Evaluation of Packed Capillary Liquid Chromatography Columns with Inner Diameters from 20 to 50 μm", *Analytical Chemistry*, vol. 61, pp. 1128-1135 (1989).

John H. Knox et al., "Effect of Column To Particle Diameter Ratio on the Dispersion of Unsorbed Solutes in Chromatograph", *Analytical Chemistry*, vol. 41, No. 12, pp. 1599-1606 (Oct. 1969).

Hookeun Lee et al., "Optimization of reversed-phase microcapillary liquid chromatography for quantitative proteomics", *Elsevier—Journal of Chromatography B*, vol. 803, pp. 101-110 (2004).

J. Andreas Lippert et al., "Fast Ultrahigh-Pressure Liquid Chromatography: On-Column UV and Time-of-Flight Mass Spectrometric Detection", *J. Microcolumn Separations*, vol. 11, No. 9, pp. 631-643 (1997).

Quanzhou Luo et al., "More Sensitive and Quantitative Proteomic Measurements Using Very Low Flow Rate Porous Silica Monolithic LC Columns with Electrospray Ionization-Mass Spectrometry", *Journal of Proteome Research*, vol. 5, pp. 1091-1097 (2006).

Quanzhou Luo et al., "Preparation of 20-μ-i.d. Silica-Based Monolithic Columns and Their Performance for Proteomics Analyses", *Analytical Chemistry*, vol. 77, No. 15, pp. 5028-5035 (Aug. 1, 2005).

John E. MacNair et al., "Ultrahigh-Pressure Reversed-Phase Liquid Chromatography in Packed Capillary Columns", *Analytical Chemistry*, vol. 69, No. 5, pp. 983-989 (Mar. 15, 1997).

Susan E. Martin et al., "Subfemtomole MS and MS/MS Peptide Sequence Analysis Using Nano-HPLC Micro-ESI Fourier Transform Ion Cyclotron Resonance Mass Spectrometry", *Analytical Chemistry*, vol. 72, No. 18, pp. 4266-4274 (Sep. 15, 2000).

V.L. McGuffin et al., "Optimization and Evaluation of Packed Capillary Columns for High-Performance Liquid Chromatography", *Journal of Chromatography*, vol. 225, pp. 381-393 (1983).

Milos V. Novotny, "New developments in bioanalytical chromatography", *Journal of Pharmaceutical & Biomedical Analysis*, vol. 7, No. 2, pp. 239-246 (1989).

Junmin Peng et al., "Proteomics: the move to mixtures", *Journal of Mass Spectrometry*, vol. 36, pp. 1083-1091 (2001).

Wei-Jun Qian et al., "Advances and Challenges in Liquid Chromatography-Mass Spectrometry Based Proteomic Profiling for Clinical Applications", *MCP Papers in Press*, Published on Aug. 3, 2006 as Manuscript M600162-MCP200.

Mikel R. Roe et al., "Gel-free mass spectrometry-based high throughput proteomics: Tools for studying biological response of proteins and proteomes", *Proteomics*, vol. 6, pp. 4678-4687 (2006).

Gerard Rozing, "Trends in HPLC Column Formats—Microbore, Nanobore and Smaller", *Recent Developments in LC Column Technology*, pp. 2-7 (Jun. 2003).

Andrea Schmidt et al., "Effect of Different Solution Flow Rates on Analyte Ion Signals in Nano-ESI MS, or: When Does ESI Turn into Nano-ESI?", *American Society for Mass. Spectrometry*, vol. 14, pp. 492-500 (2003).

Yufeng Shen et al., "Automated 20 kpsi RPLC-MS and MS/MS with Chromatographic Peak Capacities of 1000-1500 and Capabilities in Proteomics and Metabolomics", *Analytical Chemistry*, vol. 77, pp. 3090-3100 (2005).

Yufeng Shen et al., "Ultrasensitive Proteomics Using High-Efficiency On-Line Micro-SPE-NanoLC-NanoESI MS and MS/MS", *Analytical Chemistry*, vol. 756, pp. 144-154 (2004).

Richard D. Smith et al., "Ultrasensitive and Quantitative Analyses from Combined Separations—Mass Spectrometry for the Characterization of Proteomes", *Accounts of Chemical Research*, vol. 37, pp. 269-278 (2004).

Toyohide Takeuchi et al., "Micro-High-Performance Liquid Chromatography with Long Micro-Packed Flexible Fused-Silica Columns", *Journal of Chromatography*, vol. 238, pp. 409-418 (1982).

Luke Tolley et al., "Very High Pressure Gradient LC/MS/MS", *Analytical Chemistry*, vol. 73, pp. 2985-2991 (2001).

Ed van der Heeft et al., "A Microcapillary Column Switching HPLC-Electrospray Ionization MS System for the Direct Identification of Peptides Presented by Major Histocompatibility Complex Class I Molecules", *Analytical Chemistry*, vol. 70, pp. 3742-3751 (1998).

Matthias Wilm et al., "Analytical Properties of the Nanoelectrospray Ion Source", *Analytical Chemistry*, vol. 60, No. 1, pp. 1-8 (Jan. 1, 1996).

Matthias S. Wilm et al., "Electrospray and Taylor-Cone theory, Dole's beam of macromolecules at last?", *Elsevier—International Journal of Mass Spectrometry and Ion Processes*, vol. 136, pp. 167-180 (1994).

Chuanhui Xie et al., "Octadecylated Silica Monolith Capillary Column with Integrated Nanoelectrospray Ionization Emitter for Highly Efficient Proteome Analysis", *Molecular & Cellular Proteomics* 5.3, pp. 454-461 (2006).

Frank J. Yang, "Fused-Silica Narrow-Bore Microparticle-Packed-Column High-Performance Liquid Chromatography", *Journal of Chromatography*, vol. 236, pp. 265-277 (1982).

Notification of Transmittal of the International Search Report and the Written Opinion of the International Searching Authority or the Declaration for International Application No. PCT/US2008/064845 dated Jul. 23, 2008.

Supplementary European Search Report for European Application No. EP 08 76 9735 dated Sep. 14, 2011.

\* cited by examiner

CHROMATOGRAPHIC COLUMNS WITH INTEGRATED ELECTROSPRAY EMITTERS

CLAIM OF PRIORITY

This application is the National Stage of International Application No. PCT/US2008/064845, filed May 27, 2008, which claims the benefit of U.S. Provisional Patent Application Ser. No. 60/932,734, filed on Jun. 1, 2007. The contents of these applications are hereby incorporated by reference in their entireties.

TECHNICAL FIELD

This invention relates to chromatography, and more particularly to chromatographic columns with porous frits and integrated single micron and sub-micron electrospray emitters, as well as methods of making them.

BACKGROUND

Liquid chromatography (LC) is a well-established analytical technique for separating components of a fluidic mixture for subsequent analysis and/or identification, in which a column is packed with a stationary phase material that typically is a finely divided solid or gel such as small particles with diameters of a few microns. A variety of different detectors can be used to detect the analytes separated on an LC column. Additionally, the separated components may be passed from the liquid chromatography column into other types of analytical instruments for further analysis, e.g., liquid chromatography-mass spectrometry (LC-MS) separates compounds chromatographically before they are introduced to an ion source of a mass spectrometer.

Mass spectrometry ("MS") is an analytical technique used to measure the mass-to-charge ratio of gas phase ions. This is achieved by ionizing a sample and separating ions of differing masses and recording their relative abundance by measuring intensities of ion flux. Electrospray ionization (ESI) is a commonly applied ionization technique when dealing with biomolecules such as peptides and proteins. The electrospray process creates highly-charged droplets that, under evaporation, create ions representative of the species contained in a sample solution.

Mass spectrometry-based proteomics, particularly liquid chromatography coupled to electrospray ionization mass spectrometry (LC-ESI-MS), has recently become the technique of choice for rapid identification and characterization of proteins in biological systems. Moreover multiple approaches now exist to conduct these experiments in a semi-quantitative manner to monitor changes in protein expression and specific post-translational events as a function of biological perturbation. Despite its advantages discussed above, mass spectrometry suffers from limited dynamic range (e.g., the inability to detect peptides spanning an abundance ratio greater than 5000:1 in a single scan/spectrum) and finite acquisition rate (e.g., the inability to acquire MS/MS data at a rate sufficient to provide sequence information on all peptides in a complex mixture during a single LC-MS/MS run, regardless of their relative abundance). These limitations, combined with current trends towards analysis of increasingly complex mixtures (biomarkers, signaling pathways, etc) continue to push the limits of the ubiquitously used 75 μm and 100 μm I.D. (i.e., inner diameter) fused silica capillary columns packed with widely available 5 and 10 μm diameter reversed phase HPLC resins.

SUMMARY

The invention is based, at least in part, on the discovery that one can achieve exceptional LC-MS performance using chromatographic columns that include a porous yet robust silicate-based frit, a minimal dead space, and an integral electrospray emitter that has a diameter of, e.g., less than 3 microns. These columns can be used at very low flow rates, e.g., as low as 3-5 nanoliters/minute and even 1 nanoliter/minute.

In one aspect, the disclosure features methods of preparing robust fused silica-based capillary columns with integrated emitter tips, e.g., for high sensitivity LC-MS/MS analyses. The methods include: (a) obtaining a tube including two open ends and a lumen with a diameter of 75 microns or less extending between the two open ends; (b) depositing a liquid silicate composition into the tube lumen at a first open end of the tube; (c) forming a porous ceramic material from the composition in the tube lumen at a location near the first open end such that a space is formed between the ceramic material and the open end that is substantially free of the ceramic material; and (d) forming a tapered emitter having an orifice diameter of less than e.g., 3 microns at the first open end.

In another aspect, the disclosure features chromatographic columns that include a silica tube including a tapered end forming an orifice having a diameter of, e.g., less than 3 microns; a lumen having a diameter of, e.g., 75 microns or less, and a porous frit comprising silicate. The porous frit is located adjacent the tapered end within about 1 to 5 mm from the orifice and has a length of from about 1 to 3 mm.

Embodiments may include one or more of the following features. The method can include packing the tube with a slurry of beads having a diameter of about 1.8 μm to 5 μm, e.g., after forming the ceramic material. The liquid silicate composition may include lithium silicate and tetramethylammonium silicate. The ceramic material can be formed by heating the composition. The ceramic material can be formed by heating the composition to 300° C. or higher. The tapered emitter can be formed by using a laser-based pipette puller. The tapered emitter can have an orifice diameter of 1.5 microns or less. The tapered emitter can be configured to be used as an electrospray emitter.

Embodiments can also include one or more of the following features. The silicate of the chromatographic column can include lithium silicate. The orifice can have a diameter of 1.5 microns or less. The orifice can have a diameter of 0.75 micron or less. The column can be capable of withstanding a pressure of 5000 psi or higher. The column can be capable of withstanding a pressure of 7500 psi or higher, e.g., 9000 psi or higher. The orifice can be dimensioned and configured for use as an electrospray emitter in mass spectrometry. The orifice can be dimensioned and configured to operate at a flow rate of, e.g., about 10 nL/min or less. The flow rate can be 5 nL/min or less, e.g., 1 nL/min or less.

As used herein, the term "single-micron" means a dimension of larger than 1 micron and smaller than 10 microns. The term "sub-micron" means a dimension of smaller than 1 micron.

Aspects and embodiments described herein may include one or more of the following advantages. This disclosure features fabrication of fused silica based capillary HPLC columns with integrated electrospray emitter tips, which can be used in proteomics-based liquid chromatography mass spectrometry experiments. The construction of fused silica based HPLC columns with integrated electrospray emitter tips decreases dead volume between the HPLC column bed and emitter tip and thus improves chromatographic performance. The in situ formation of column bed retention frits in fused silica capillaries of any size, especially of small I.D., facilitates construction of small-inner diameter HPLC capillaries with arbitrarily small electrospray emitter tips. In addition, the methods disclosed herein can be used in conjunction with so-called ultra-high pressure LC, which offers further improvements in chromatographic performance. For example, the new columns with integrated electrospray emitters made by the methods disclosed herein can withstand ultra high pressures, e.g., 5000 psi or higher, 7500 psi or higher, 9000 psi or higher, and even 10,000 psi or higher.

This disclosure also features columns made by the disclosed methods, which have arbitrarily small inner diameters and have porous retention frits that are mechanically stable, but still allow sufficient volumetric flow to facilitate packing of particulate LC beds and have mechanical stability sufficient to withstand ultra-high pressure LC and facilitate placement of integrated emitter tips close to the frit and with arbitrarily small orifice diameters. Particularly, devices with 25 micron-inner diameter capillary columns, packed with 3 micron diameter HPLC resin, terminating with an electrospray emitter tip of less than 1 micron diameter, at flow rates of less than 1 nanoliter per minute have been fabricated and operated successfully applying the methods disclosed herein. In comparison, for example, the smallest devices currently offered commercially, e.g., those offered by New Objective, Inc., have 50 micron inner diameters, are packed with 5 micron diameter resin beads, terminate with a 10 micron emitter tip, and are intended to operate at flow rates of 50-100 nL/min.

Without being bound by theory, it appears that no one has successfully demonstrated a method to fabricate columns that allow experimental exploration of ultra-small scale LC-MS regimes to date, because of the difficulties discussed below. Generally, if columns interfaced to electrospray ionization benefit significantly by having an integrated ESI emitter on the column, preferably immediately adjacent to the column frit. Electrospray ionization efficiency increases as effluent flow rate decreases. However, stable electrospray at very low flow rates (e.g., 10 nL/min or less) requires exceedingly small diameter orifices (e.g., less than 10 µm). Further, the Van Deemter equation predicts that at flow rates below Van Deemter plot minimums, longitudinal diffusion is expected to lead to band broadening. Moreover, the introduction of dead-volume between the frit and emitter tip further contributes to band broadening. As a result, the chromatographic band broadening may be expected to cancel out any gains realized by improved ionization efficiency. Surprisingly, however, use of the new columns with integrated single- or sub-micron electrospray emitters described in this disclosure has led to significantly increased LC-MS performance.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

FIG. 3d is an electron micrograph of an integrated electrospray emitter formed on the fused silica tube, and FIG. 3e is an electron micrograph of a cross-section of the column of FIGS. 3a-3d showing the porous frit formed in the tube.

DETAILED DESCRIPTION

This disclosure features a simple strategy to construct robust fused silica-based capillary columns with integrated, porous silicate-based frits and single- or sub-micron emitter tips for high sensitivity LC-MS/MS analyses. This approach can use commercially available, economical starting materials, along with a simple and rapid procedure, which enables rapid column construction, e.g., in less than 30 minutes. These columns can be readily used with conventional- and high-pressure (e.g., 5000 psi or higher) binary HPLC systems. LC peak widths (e.g., full width at half maximum, "FWHM") of less than 30 seconds at separation flow rates of about 3-5 nanoliters per minute ("nL/min") can be routinely observed from these HPLC column assemblies. When appropriately stored, columns of 25 µm I.D. with integrated ESI emitters of 1.5 µm or smaller diameter can be used for several weeks without failure. Further, analysis of tryptic peptides derived from whole cell lysate clearly demonstrates the improved MS performance (e.g., 10-fold or higher increase of signal-to-noise ratio) realized through the combination of miniaturized column assemblies and ultra-low LC flow rates.
Chromatographic Columns with Porous Frits and Integrated Electrospray Emitters The new columns are the result of carefully balancing a variety of parameters to achieve significant performance enhancements. The columns have a small inner diameter ranging from about 5 to about 75 microns, e.g., about 10 to 25 microns. The columns are filled with small resin particles or beads of 1.8, 2, 3, 4, or 5 microns. The columns include an integral emitter having an orifice of under 3 microns, e.g., 2, 1.5, 1.0, or even smaller. These combinations of dimensions and the use of a robust, silicate-based porous frit enable the new columns to be used at extremely low flow rates, e.g., under 10 nanoliters/minute, e.g., under 7.5, 5.0, 4.0, 3.0, 2.0, 1.0, and even less than 1.0 nanoliter/minute. In addition, the new columns are surprisingly robust, operating well at high pressures, such as pressures at or above 5000, 7000, 9000, 9500, and even 10,000 psi.

Figure 1:
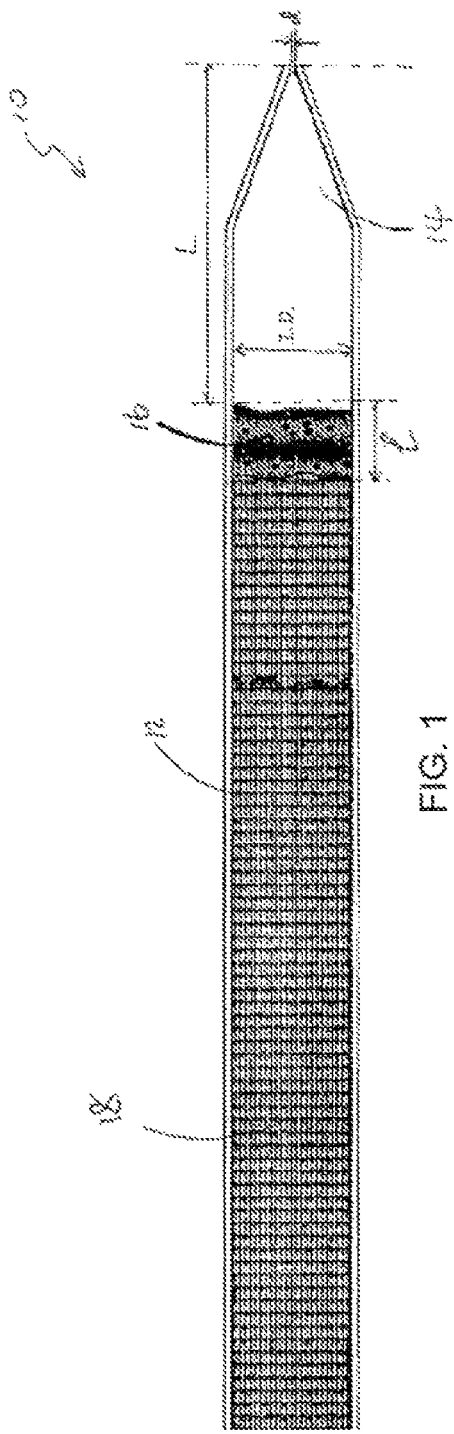
FIG. 1 is an enlarged cross-sectional view of a portion of a chromatographic column.

As shown in FIG. 1, a capillary tube 10 used in LC-ESI-MS includes a tubular body 12 of uniform inner diameter ("I.D.") and a tapered end 14, which has an orifice of a diameter "d." Tube 10 can accommodate a sorbent bed or solid phase 18 that is defined by the wall of the body 12. A porous retention frit 16 formed of, e.g., silicate, separates the sorbent bed 18 and the tapered end 14.

The capillary tube 10 can have I.D. in the range of from about 5 micron to about 2 mm, e.g., 5 to 75 microns, 10 to 50 microns, or 15 to 25 microns. The diameter d of the orifice of the tapered end 14 can range from a few hundred nanometers to about a few microns, e.g., from 0.5 to 3 microns or 0.5 to 1.5 microns. The frit 16 adheres to the smooth inner wall surface of the tube 10 and is located back from the orifice at a distance "L" which varies from 2 mm to 5 mm. The frit 16 also has a length "l" that varies from about 0.5 mm to 2 mm. The sorbent bed 18 is normally injected under high pressure into the tube 10 in the form of a slurry subsequent to forming the frit 16. Since the frit is porous, a slurry of sorbent 18 can be easily injected into the tube 10.

The empty capillary tubes used for HPLC columns are those known in the art, and can, for example, be made of ceramic materials, such as borosilicate glass, fused-silica, polyimide coated fused-silica and aluminum coated fused-silica; metals, such as stainless steel, glass-lined stainless steel or silica lined stainless steel; or they can be made of polymeric materials or fused silica-lined polymeric materials. The polymeric material that can be used include fluoropolymers, such as ethylene tetrafluoroethylene (ETFE), fluorinated ethylene propylene (FEP) and polytetrafluoroethylene (PTFE); polyolefins, such as high density linear polyethylene (HDPE), low-density linear polyethylene (LDPE) and polypropylene; polyketones, such as polyetheretherketone (PEEK) and silica-lined PEEK; acrylics, such as polymethylmethacrylate (PMMA), polyamides, such as nylon 6, nylon 11 and nylon 12; and polyimide. Useful capillary tubes for use as capillary columns in accordance with the present disclosure are those of, stainless steel, PEEK and HDPE, and polyimide-coated fused silica.

The internal or external shapes of capillary columns can have a variety of regular geometric shapes, such as round, oval, square, rectangular, polygonal, such as pentagonal, hexagonal, and the like; or can have irregular shapes. The term "internal shape" of the capillary columns, as used herein, has the same meaning as the "bore" of a capillary column. Tubes commonly used for these columns have a round internal shape or bore.

General Methodology of Making the Chromatographic Columns

FIGS. 2a-2e illustrate an exemplary method to make the new fused silica capillary columns with silicate-based frits and integrated emitter tips. As formed, the columns with integrated emitters can be used in LC-ESI-MS experiments.

Forming Porous Frits in Silica Tubing

Figure 2:
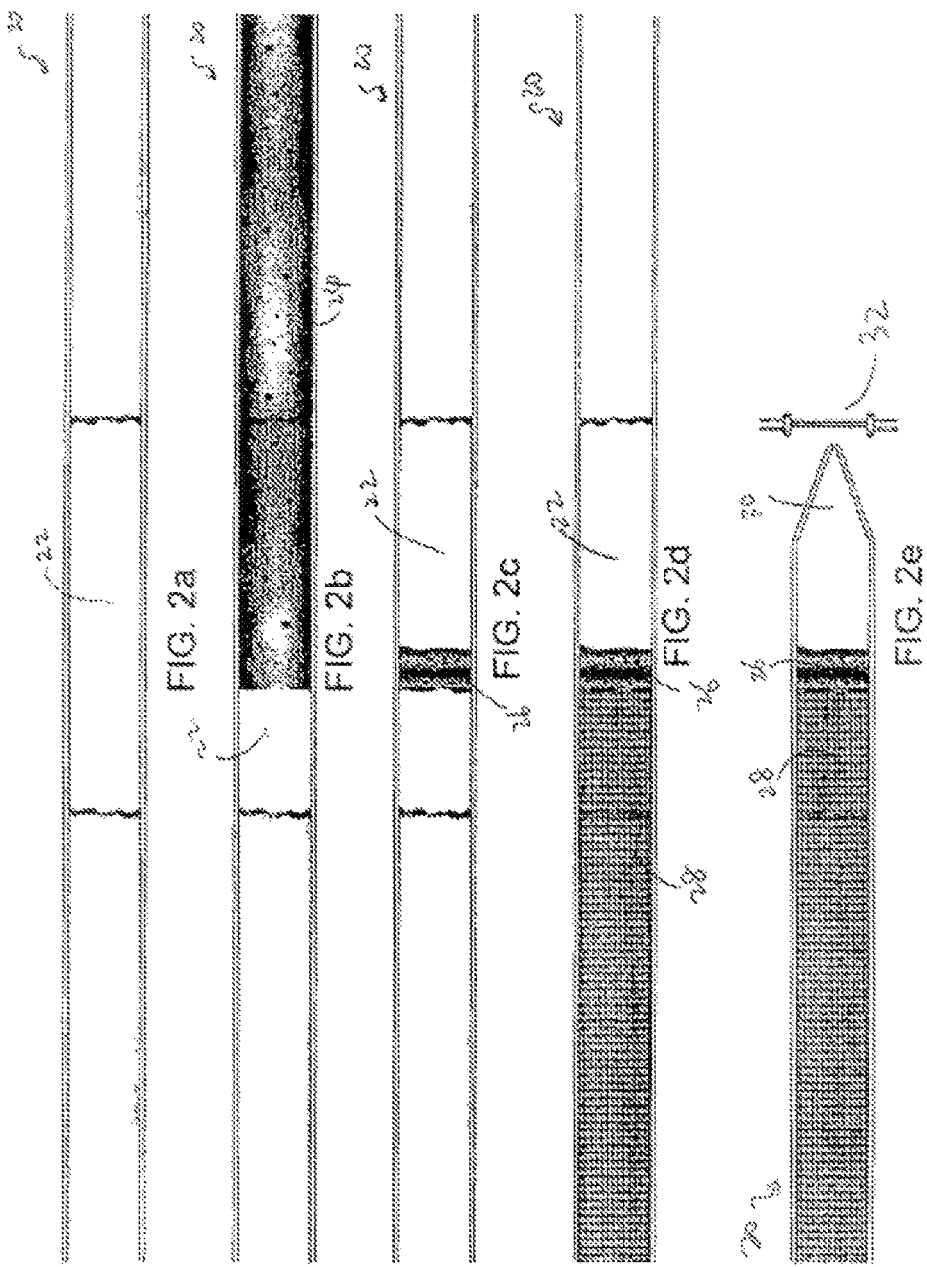
FIGS. 2a-2e are schematic representations in cross-section of intermediate columns during various steps of an exemplary method of making chromatographic columns with integrated electrospray emitters.

As shown in FIG. 2a, a small section 22 (e.g., 1.5 cm) of fused silica is exposed by removing a polyimide coating (show in light grey), for example, via torch heating near one end of a polyimide-coated used silica capillary tube 20. Next, referring to FIGS. 2b and 2c, a frit-forming precursor 24 such as a potassium and lithium silicate solution (shown dark grey with a few circles and dots) is drawn up to the fused silica window 22 by capillary action. A soldering iron (not shown) at about 300° C. is brought close to the section 22 and the focused heat induces local polymerization of the precursor 24 to form a porous frit 26 approximately at the leading edge of the silicate solution with a confined length "l" usually in the range of 1 to 2 mm. Any unpolymerized silicate solution is then expelled from the capillary by pressurized rinse with an aqueous solution.

In particular embodiments, tetramethylammonium silicate is added to the potassium and lithium silicate solution in an effort to better control the pore size of the frit. Without wishing to be bound by theory, it is believed that the pore size is determined, in part, by the size of the cation in the silicate solution. Tetramethylammonium is a larger cation compared to potassium and lithium cations, therefore the average pore size can be increased by increasing the abundance of tetramethylammonium silicate in the silicate solution. The volume ratio of the tetramethylammonium silicate solution to the potassium and lithium silicate solution is preferably from about 2:1 to 1:3, e.g., about 1:2. For example, a frit-forming precursor solution can be made by mixing a 50 μL tetramethyl ammonium silicate (15-20 wt. %) aqueous solution, a 100 μL Klebofon™ 1524 silicate solution (e.g., of approximately 77.0 wt % water, 2.5 wt % $Li_2O$, and 20.5 wt % $SiO_2$), and a 10 μL, formamide. Unexpectedly, besides the benefit of pore-size control, mixing tetramethylammonium silicate and lithium silicate solution also allows creation of remarkably robust frits. As a result, the robust frit is less likely to shed fine particulates that may clog the pores of the frit and/or the orifice when high pressure is applied to the LC column. As an example, the robustness of the frits made as described herein is evidenced by several weeks of repeated use of the LC column with integrated emitter tips of less than 1.5 μm in diameter, at column flow rates of e.g. 3-5 nL/min.

The robustness of the frits is further evidenced by the fact that the new columns with integrated electrospray emitters made by the methods disclosed herein have been tested to withstand ultra high pressures, e.g., over 5000, 7500, 9000, and 9500 psi.

Packing the Chromatographic Column

After the frit 26 is formed, a slurry formed of sorbent 28 or particles of specified diameter (e.g., Monitor 3 μm diameter, 120 Å pore size C18 particles) and a mobile phase (e.g., an organic solvent) is injected under pressure from the column end opposite to where the silicate entered the column, as illustrated in FIG. 2d. In some embodiments, pressure packing the LC resin 28 can also be used to simultaneously expel the unpolymerized silicate. More detail of packing chromatographic columns is described in Yang, U.S. Pat. No. 4,483, 773.

Forming Single-Micron Electrospray Emitters

After the column 20 is packed with sorbent bed 28, the column can be dried with pressurized gas, such as helium, for a few minutes and an integrated emitter tip of sub- or single micron diameter, e.g., 0.5-1.5 μm can be formed using a laser-based pipette puller, such as the P-2000 of Sutter Instruments Company, Calif. Referring now to FIG. 2e, the packed capillary 20 is placed into a laser-based pipette puller and a small diameter orifice emitter tip is then pulled 2-5 mm from the frit 26. The orifice diameters of these emitters can range from less than 3 microns down to 2.5, 2.0, 1.5, 1.0, or even less than 1 micron.

Storing the Packed Columns with Integrated Emitters

For convenient handling and storage, the column can be sheathed in a TEFLON® tubing (e.g., 0.062 inch O.D.× 0.0115 inch I.D.) that is counter-bored (0.038 inch I.D.) at one end using a pin vise drill to provide a protective cover for the tip when not in use. For extended storage, the column may be placed into a conical style tube (TEFLON® sleeve oriented downward) containing 5 mL of dilute acetic acid. Without wishing to be bound by theory, it is believed that this procedure keeps the emitter tip bathed in liquid such that trace quantities of nonvolatile salts that may be present in the HPLC solvents do not precipitate on the tip. Alternately, the column may be dried by expelling all liquids with pressurized helium.

EXAMPLES

The following examples are illustrative, but not limiting.
Starting Materials for Making the Chromatographic Column Assemblies Fused-silica tubing is available, e.g., from Polymicro Technologies (Phoenix, Ariz.). Various polyetheretherketone ("PEEK") nuts, ferrules, and other fittings are available, e.g., from Valco Instrument Co. (Houston, Tex.) and Upchurch Scientific (Oak Harbor, Wash.). TEFLON® tubing was purchased from Zeus Industrial Products (Orangeburg, S.C.). Bulk resins for reversed phase chromatography (Monitor 5 µm diameter, 120 Å pore size C18 particles; Monitor 3 µm diameter, 120 Å pore size C18 particles) can be obtained, e.g., front Column Engineering (Ontario, CA). Other resins can be used interchangeably depending on the specific use of the chromatographic columns as is known in this field.

Frit-forming compounds or precursors such as potassium and lithium silicate solutions can be obtained commercially, e.g., from PQ Corporation (Valley Forge, Pa.). Formamide, tetramethylammonium silicate, glacial acetic acid are available, e.g., from Sigma-Aldrich (St. Louis, Mo.). HPLC grade acetonitrile can be purchased from Fisher Scientific Intl. (Hampton, N.J.).

Example 1

Forming Silicate-Based Frits in Analytical Columns

Analytical columns ("AC") were constructed from 360 µm O.D.×50 µm I.D. and 360 µm O.D.×25 µm I.D. fused silica capillary tubing. A 2.5 cm section of polyimide was removed approximately 3 cm from one end of the fused silica tubing. Silicate-based frits were cast in situ following the general protocol described above. 50 µL of tetramethylammonium silicate (Sigma-Aldrich, part#438669) was added to a microcentrifuge tube, followed by the addition of 100 µL of lithium silicate (Klebofon™ 1524 from PQ Corporation, Valley Forge, Pa.). This solution was briefly stirred, with subsequent addition of 10 µL of formamide (Sigma-Aldrich, part# F5786) followed by another brief stirring at room temperature. This solution was allowed to migrate approximately 1 cm into one end of the fused silica tubing by capillary action.

Figure 3:
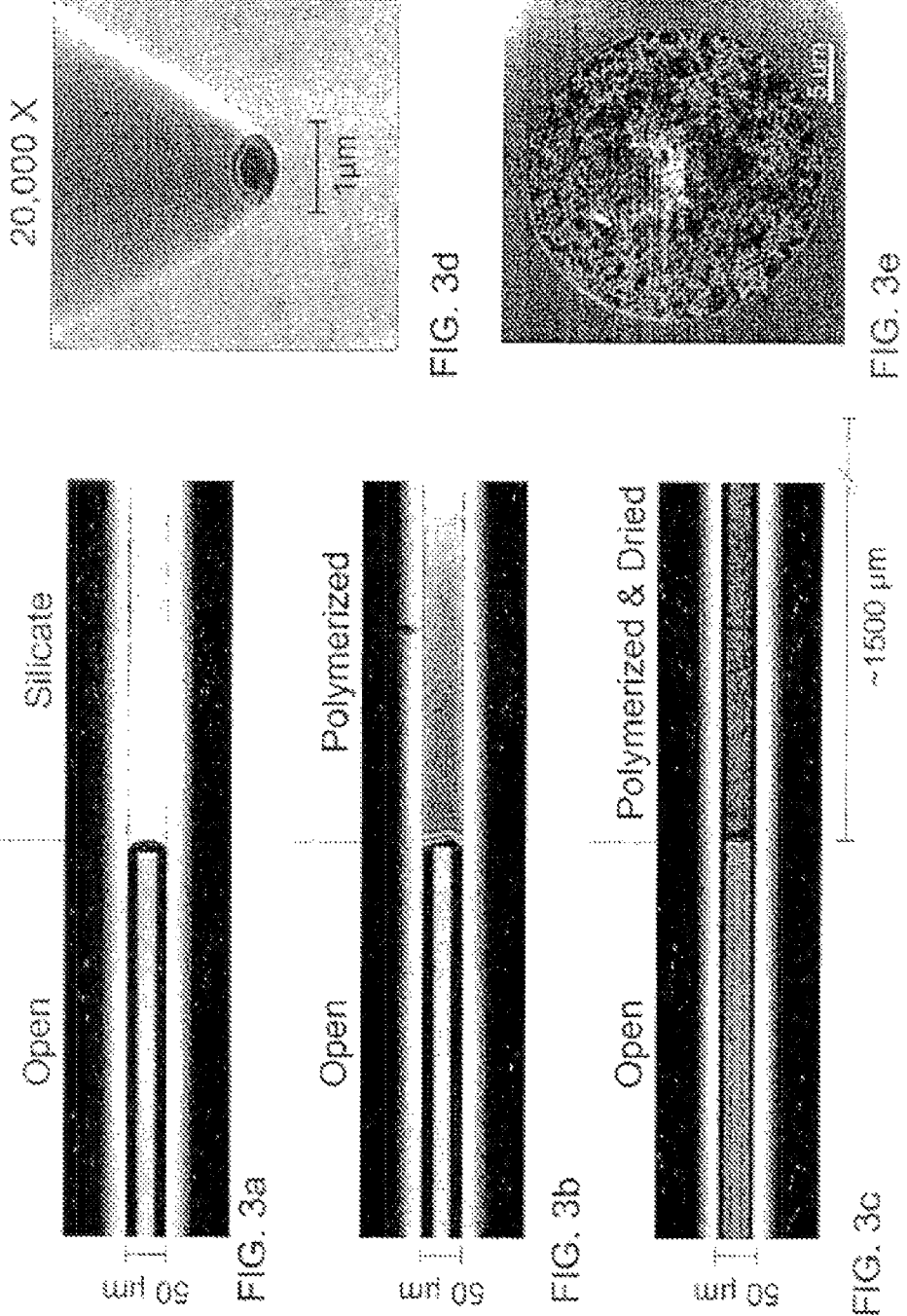
FIGS. 3a-3e are representations of intermediate columns during discrete steps for in situ formation of a frit in a fused silica tube.

Next, a variable temperature soldering iron was set to 375° C. and used to induce polymerization of the silicate solution beginning at the opposite end of the silicate plug. By slowly rotating the fused silica capillary and positioning the soldering iron immediately adjacent to the distal end of the silicate plug, gradual polymerization was easily visualized and frits of 2-5 mm in length were readily cast in 5-20 seconds. Immediately after frit formation unpolymerized silicate was ejected from the capillary by a pressurized rinse with an aqueous solution of 0.1% acetic acid. Excess fused silica tubing was trimmed using a tile scribe so that the frit was positioned at the very end of the fused silica capillary. FIGS. 3a-3c are optical images that show discrete steps in this process for construction of 50 µm I.D. analytical columns. First, the silicate solution was allowed to migrate to four fifths the length of the exposed window (FIG. 3a). Next, polymerization was induced using the soldering iron as described above, with care taken to form frits of 1-2 mm in length (FIG. 3b). After ejection of excess silicate solution the frits were re-heated with the soldering iron at 400° C. for several seconds (FIG. 3c). The re-heating can provide extra mechanical stability to the silicate-based frits. FIG. 3e is a scanning electron micrograph that shows a cross-section of the capillary tube (25 µm I.D.) filled with the mesoporous frit as formed.

Example 2

Packing the Analytical Columns

To pack the columns described in Example 1, a dense slurry of reversed phase resin was made in 1 mL, of acetonitrile and pressure packed behind the frit at pressures of approximately 500-1500 psi. A bed length of 6-8 cm was achieved in less than 10 minutes (5 µm diameter beads used for the 50 µm I.D. AC and 3 µm diameter beads used in the 25 µm I.D. AC).

Example 3

Forming Single and Sub-Micron Electrospray Emitters on Analytical Columns

The packed ACs in Example 3 were dried with pressurized helium for 5 minutes before an integrated emitter tip of 0.75-1.5 µm diameter was formed 2-4 mm beyond the frit using a laser-based pipette puller (P-2000, Sutter Instruments Company, Calif., program settings: Heat=500, Fil=0, Vel=5, Del=130, Pull=25). A Nikon I.C.-66 microscope (Micro Optics, Fresh Meadows, N.Y.) was used at 1000× or 1500× magnification for visual confirmation of tip diameter. FIG. 3d shows a high resolution electron micrograph image of a sub-micron integrated emitter tip as formed in this procedure.

Example 4

Using AC in Liquid Chromatography Mass Spectrometry Analysis

A Waters® NanoAcquity (Waters Corp., Milford, Mass.) and an Agilent 1100 series binary pump (Agilent Technologies, Santa Clara, Calif.) were used to generate solvent gradients for online LC-MS experiments. Samples were manually pressure loaded onto a precolumn (a fritted 360 µm O.D.×100 µm I.D. or 360 µm O.D.×50 µm I.D. fused silica capillary tubing packed with 5 µm diameter beads), which was then inserted into one outlet arm of a PEEK Y-style connector. The inlet and second cadet of the PEEK Y were connected to the HPLC effluent and waste lines, respectively. The base HPLC flow rate was set at 200 µL/min, and an adjustable restrictor was inserted into the waste line to provide variable backpressure (and hence flow) through the AC made in Example 3.

Typically 60-80 bar backpressure measured at the binary pump provided flow rates of 2-10 nL/min through the PC and AC. Final flow rate for each experiment was estimated from measurement of the displaced volume spanning the PC and AC, and the observed delay time for breakthrough of the organic gradient (resulting in sharp rise of the total ion chromatogram baseline) during LC-MS analysis. An Upchurch micro union with 9 nL internal swept volume was used to connect the pre- and analytical columns. The emitter tip position with respect to the mass spectrometer inlet was controlled by a NanoESI Source (Proxeon Biosystems A/S, Odense, Denmark). HPLC solvent A was 0.2 M acetic acid and solvent B was 70% acetonitrile/0.2 M acetic acid. The solvent gradient was ramped 0%-100% B in 50 min. Mass spectrometry data acquisition was performed in data-dependent mode on a hybrid linear ion trap-Orbitrap instrument (ThermoFinnigan, San Jose, Calif.) under the following conditions: MS scan, 350≤m/z≤1500; top 8 most abundant MS/MS scans with exclusion list and 3 Da width isolation window; 1.5 kVolt ESI voltage; 200° C. capillary temperature.

Mascot Daemon was used to extract and format MS/MS data for subsequent search against human IPI protein database (Mascot version 2.0.00, Matrix Science, Inc., London, United Kingdom). The search parameters allowed 2 missed cleavages for trypsin and a fixed modification of +57 corresponding to carboxyamidation of cysteine. A mass tolerance was 1.2 Da for precursors and 0.35 Da for fragment ions was specified. Only those peptide sequence identifications common between analyses performed with the large and small column assemblies, and with score ≥20 were exported from Mascot for further analysis. Selected ion chromatograms for 100 of these precursors were generated and then compared in terms of maximum precursor intensity and chromatographic peak width, measured base-to-base. Finally, manual comparison of the corresponding MS/MS spectra was performed to confirm comparison of identical precursors.

The chromatographic columns with single and sub-micron integrated electrospray emitters and methods of making such columns allow improved ionization efficiency and thus improved LC-MS performances. Emitter tips in this sub-micron size regimen readily support flow rates below 10 nL/min, and offer the potential for improved detection limits as a result of increased. More advantages are demonstrated below.

Figure 4:
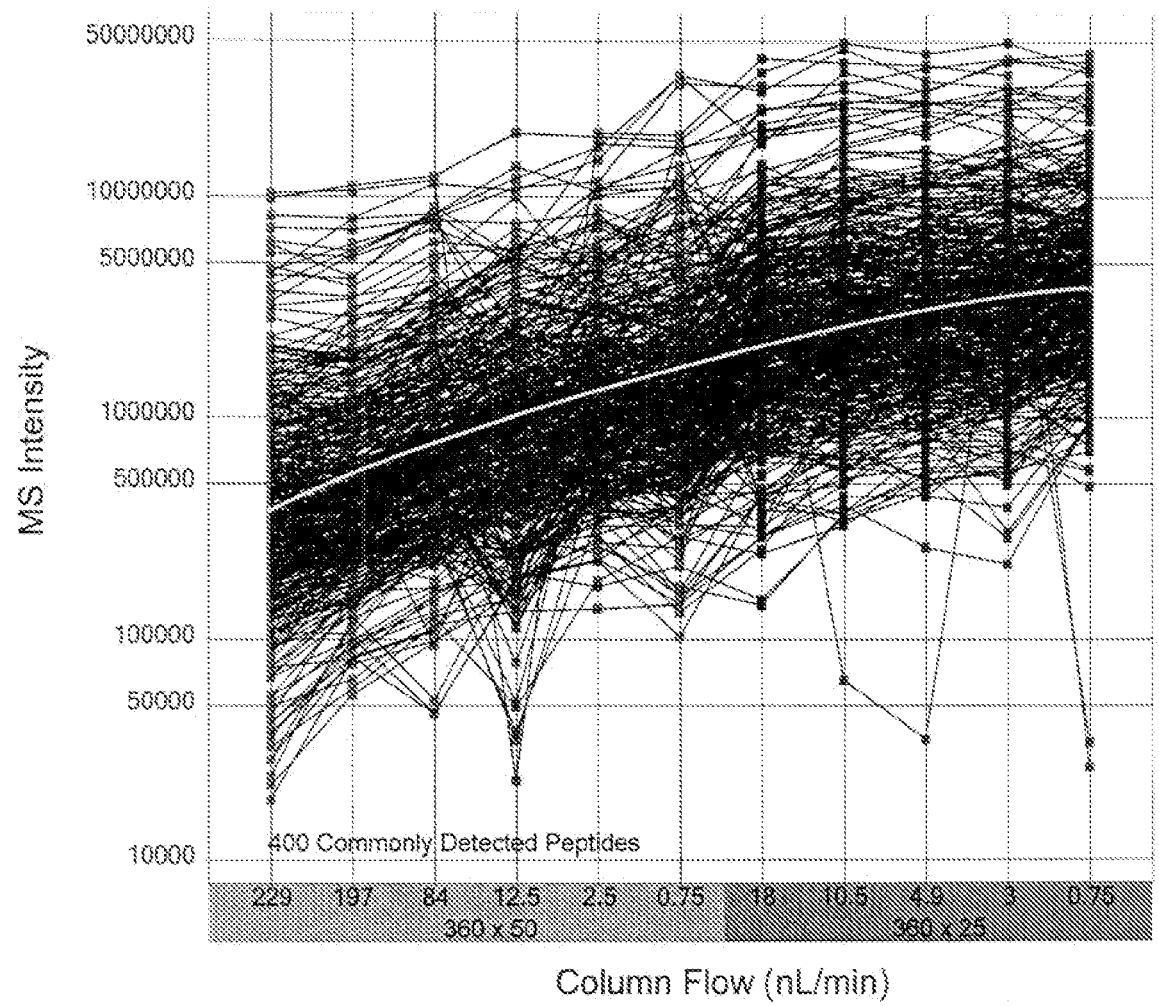
FIG. 4 is a graph of mass spectral peak intensity plotted as a function of column size and column flow rate for 400 common peptides detected using the columns described herein.

Referring particularly to FIG. 4, a plot of mass spectral peak intensity as a function of column size (red: 360 µm OD×50 µm ID: blue: 360 µm OD×25 µm ID) and column flow rate (listed above each column size, nL/min) for 400 common peptides detected across these conditions is shown. The yellow line shows the average peptide intensity observed across these column and flow rate conditions. Clearly the observed peptide intensity shows a strong and inverse correlation to the combination of column size and flow rate. For example, the average peptide intensity using 25 micron ID column tested at flow rate of 0.75 nL/min is at least ten-fold higher than that using 50 micron ID column at flow rate of 200 nL/min. In this example, both columns have emitters of 0.75-1 µm in orifice diameter.

Figure 5:
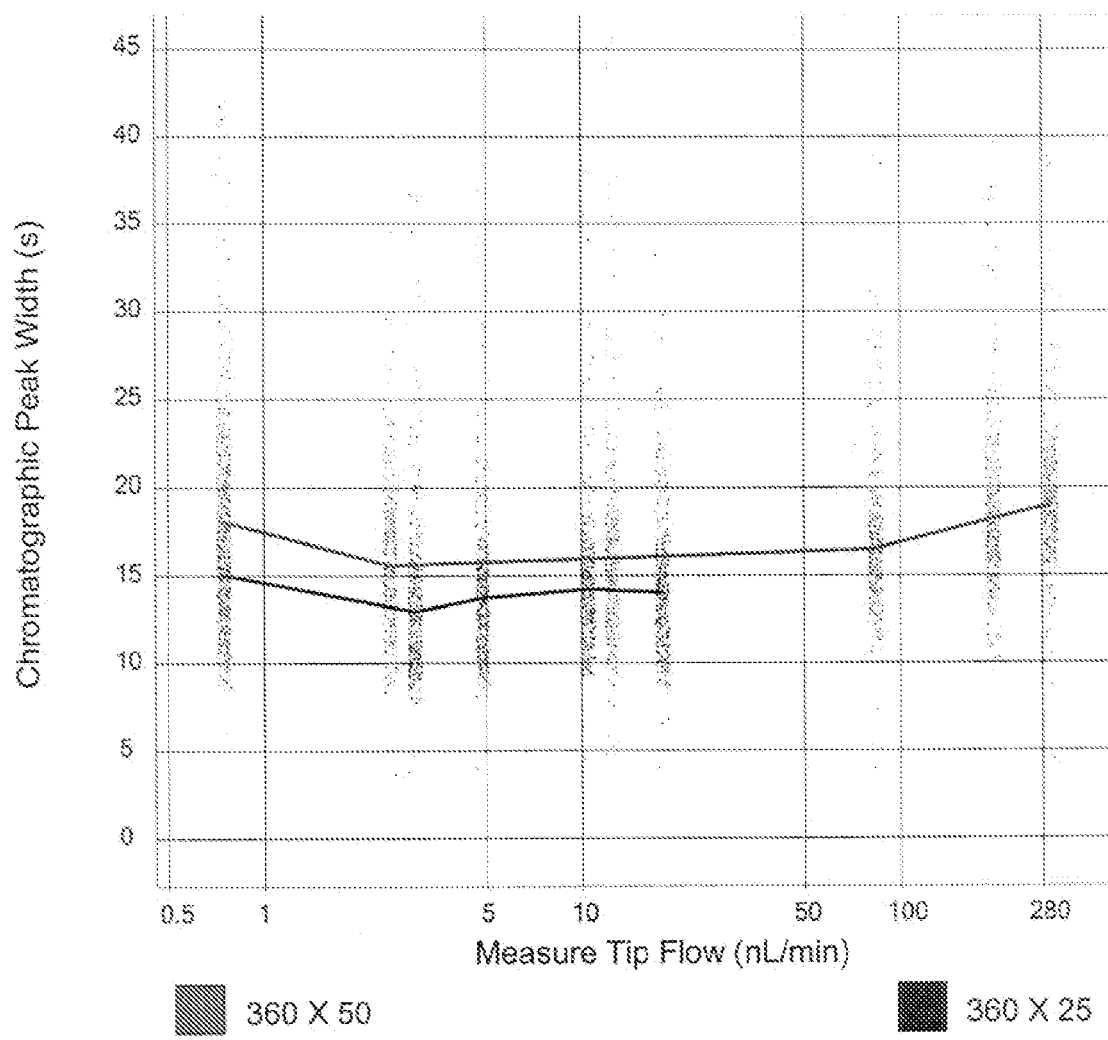
FIG. 5 is a graph of chromatographic peak width plotted as a function of column flow rate generated using the columns described herein.

Referring now to FIG. 5, chromatographic peak width (seconds) is plotted as a function of column flow rate (nL/min). Individual points are those peptides detected with large (360×50) and small (360×25) column sets. Mean chromatographic peak widths are indicated by the red (360×50) and blue (360×25). The small column set provides superior chromatographic performance at all flow rates used in this study. Furthermore, at flow rates below approximately 3 nL/min., chromatographic peak widths begin to broaden for both large and small column sets. In spite of this peak broadening, the new columns still provide a significant performance improvement.

Figure 6:
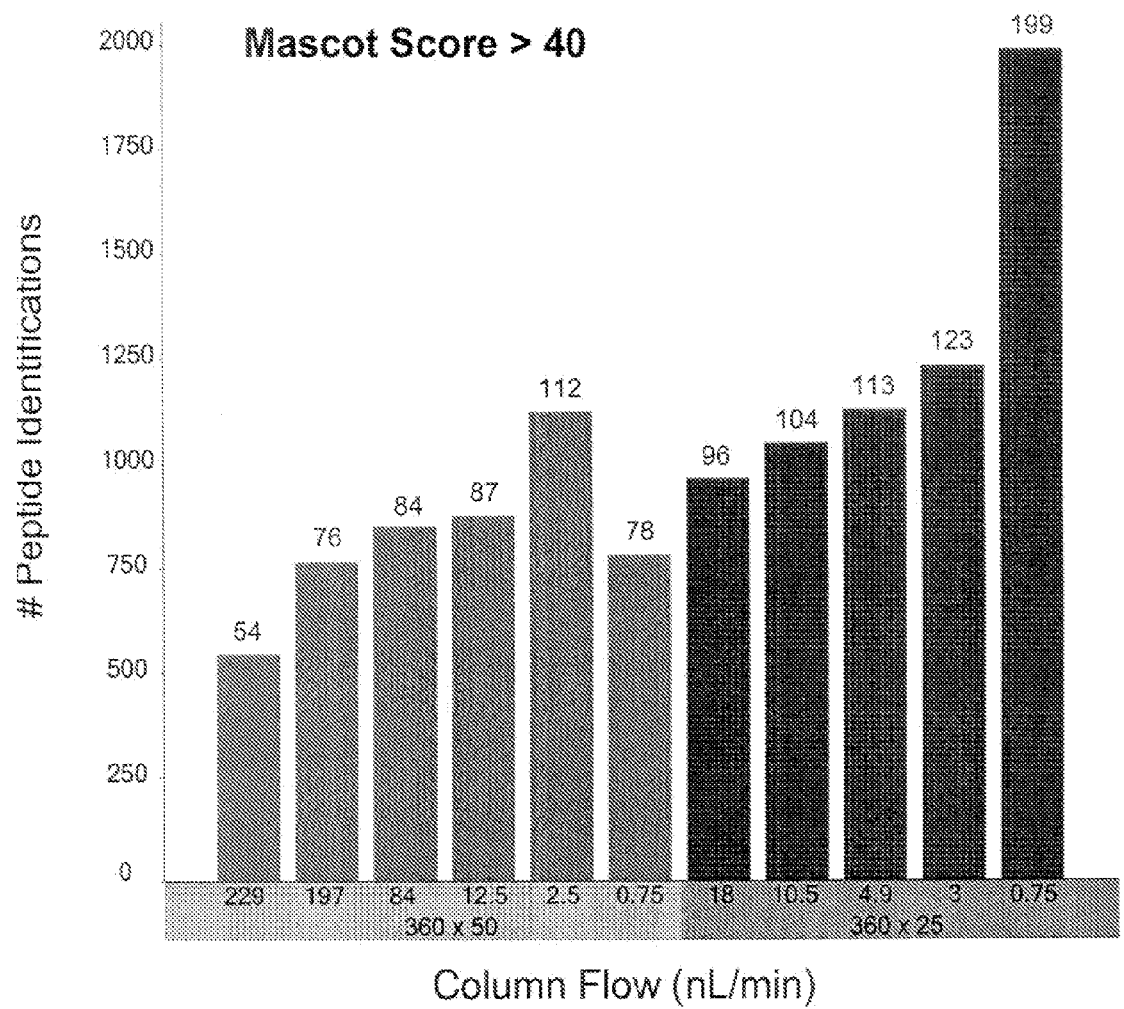
FIG. 6 is a histogram of number of peptides identified by MS/MS plotted as a function of column size and column flow rate.

Referring to FIG. 6, the number of peptides identified by MS/MS, with Mascot score ≥40, is plotted as a function of column size (red: 360 µm OD×50 µm I.D.; blue; 360 µm OD×25 µm ID) and column flow rate (listed above each column size, nL/min). Clearly the number of peptides identified per LC-MS analysis shows a strong and inverse correlation to the combination of column size and flow rate. Interestingly, for the large column set, longitudinal band broadening reduces the number of peptides identified at the lowest flow rate. In the small columns, equivalent volumetric flow yields four-times higher linear velocity, hence negating the deleterious effects of longitudinal diffusion. As a result the total number of peptides identified using the small columns continues to increase as volumetric flow decreases.

Figure 7:
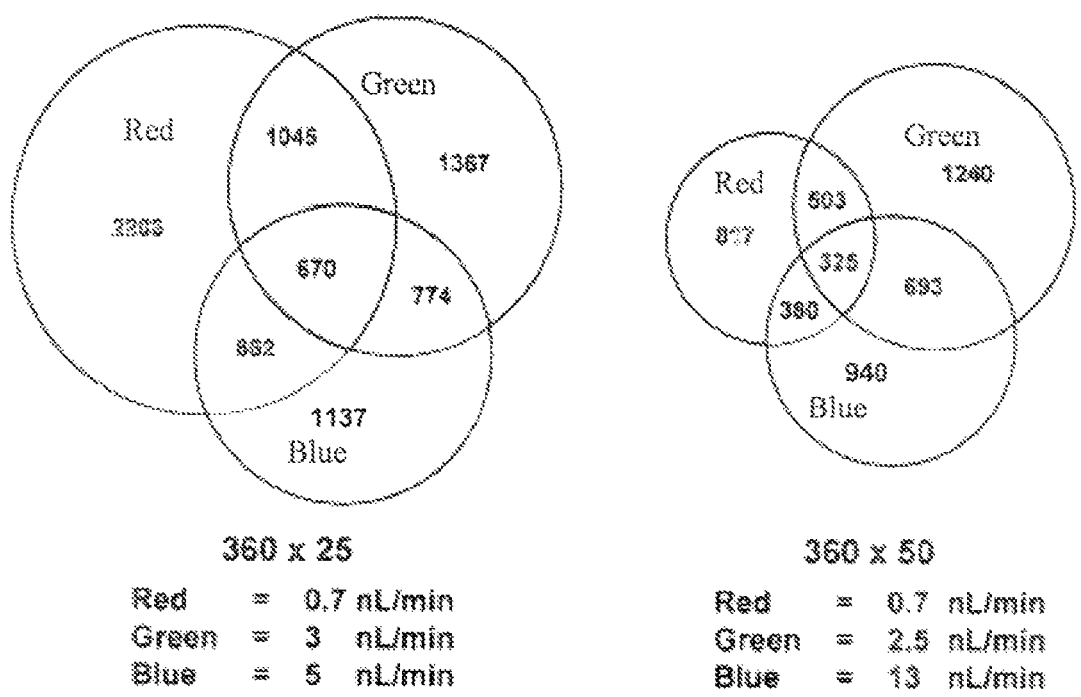
FIG. 7 is a series of Venn diagrams that show the reproducibility of peptide identifications observed for LC-MS/MS analyses.

FIG. 7 illustrates the reproducibility of peptide identifications observed for LC-MS/MS analyses across the three lowest flow rates used for the small (left) and large (right) column sets. Here, the small column set has an I.D. of 25 µm and an orifice diameter of about 0.75-1 µm while the large column set has an I.D. of 50 µm and an orifice diameter of about 0.75-1 µm µm. Taking the left Venn diagram (using 25 µm I.D. column and about 0.75-1 µm diameter orifice) for example, the largest circle indicates that 2206 species (e.g., peptides) were detected at a flow rate 0.7 nL/min, and the intermediate circle indicates that 1367 species were detected at a flow rate of 3 nL/min. The overlap of the two circles indicate the number of common species that were both detected at the two different flow rates, which in this case is 1045 common peptides. Similarly, the overlap of the three circles indicates the number of common species that were detected at three different flow rates. Generally, the higher the number of common species is, the more reproducible of peptide identification is. The Venn diagrams clearly show a more than two-fold improvement (670 vs. 325) in the number of common peptides observed, therefore clear demonstrate that smaller column set has higher reproducibility of peptide identifications.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of fabricating a chromatographic column, the method comprising:
    (a) obtaining a tube comprising first and second open ends and a lumen with a diameter of 75 microns or less extending between the two open ends;
    (b) depositing a liquid silicate composition into the tube lumen at the first open end of the tube;
    (c) forming a porous ceramic material from the composition in the tube lumen at a location near the first open end and opposite to the second open end such that a space is formed that is substantially free of the ceramic material between the ceramic material and the first open end;
    (d) forming a sorbent bed in the tube lumen; and
    (e) forming a tapered emitter having an orifice with a diameter of less than 3 microns at the first open end.

2. The method of claim 1, wherein the ceramic material is formed by heating the composition.

3. The method of claim 2, wherein the ceramic material is formed by heating the composition to 300° C. or higher.

4. The method of claim 1, wherein the tapered emitter is formed by using a laser-based pipette puller.

5. The method of claim 1, wherein the tapered emitter has an orifice diameter of 1.5 microns or less.

6. The method of claim 5, wherein the tapered emitter is configured to be used as an electrospray emitter.

7. The method of claim 1, wherein the liquid silicate composition comprises lithium silicate and tetramethylammonium silicate.

8. The method of claim 1, further comprising packing the tube with a slurry of beads having a diameter of about 1.8 µm to 5 µm after forming the ceramic material.

9. The method of claim 1, wherein:
    the tube is formed of silica; and the porous ceramic material forms a porous frit, wherein the porous frit is located adjacent the tapered emitter within 1 to 5 mm from the orifice and has a length of from about 1 to 3 mm.

10. The method of claim 9, wherein the silicate comprises lithium silicate.

11. The method of claim 9, wherein the orifice has a diameter of 1.5 microns or less.

12. The method of claim 9, wherein the orifice has a diameter of 0.75 micron or less.

13. The method of claim 9, wherein the column is capable of withstanding a pressure of 5000 psi or higher.

14. The method of claim 9, wherein the column is capable of withstanding a pressure of 7500 psi or higher.

15. The method of claim 9, wherein the column is capable of withstanding a pressure of 9000 psi or higher.

16. The method of claim 9, wherein the orifice is dimensioned and configured for use as an electrospray emitter in mass spectrometry.

17. The method of claim 16, wherein the orifice is dimensioned and configured to operate at a flow rate of 10 nL/min or less.

18. The method of claim 17, wherein the flow rate is 5 nL/min or less.

19. The method of claim 17, wherein the flow rate is 1 nL/min or less.

20. The method of claim 9, further comprising forming the tapered emitter after forming the porous ceramic material and the sorbent bed in the tube lumen.

21. The method of claim 9, wherein the porous ceramic material and the sorbent bed are formed of different materials.

22. The method of claim 9, further comprising:
    forming the sorbent bed from a material different from the liquid silicate composition; and
    forming the tapered emitter after forming the porous ceramic material and the sorbent bed in the tube lumen.

23. The method of claim 1, further comprising forming the tapered emitter after forming the porous ceramic material and the sorbent bed in the tube lumen.

24. The method of claim 1, wherein the porous ceramic material and the sorbent bed are formed of different materials.

25. The method of claim 1, further comprising:
    forming the sorbent bed from a material different from the liquid silicate composition; and
    forming the tapered emitter after forming the porous ceramic material and the sorbent bed in the tube lumen.

* * * * *